United States Patent [19]

Oka

[11] Patent Number: 6,017,739
[45] Date of Patent: Jan. 25, 2000

[54] METHOD AND NUCLEIC ACID-CONCENTRATING ASSAY KIT FOR CONCENTRATING MUTANT NUCLEIC ACID

[75] Inventor: Takanori Oka, Takata-gun, Japan

[73] Assignee: Wakunga Seiyaku Kabushiki Kaisha, Osaka, Japan

[21] Appl. No.: 09/029,981

[22] PCT Filed: Sep. 13, 1996

[86] PCT No.: PCT/JP96/02617

§ 371 Date: Mar. 13, 1998

§ 102(e) Date: Mar. 13, 1998

[87] PCT Pub. No.: WO97/10359

PCT Pub. Date: Mar. 20, 1997

[30] Foreign Application Priority Data

Sep. 13, 1995 [JP] Japan ..................................... 7-260883

[51] Int. Cl.[7] .............................. C12P 19/34; C12Q 1/68; C07H 21/04
[52] U.S. Cl. .............................. 435/91.2; 435/6; 435/7.1; 435/91.1; 435/91.21; 536/24.3; 536/24.31; 536/24.32; 536/24.33
[58] Field of Search .................................. 435/6, 7.1, 91.1, 435/91.2, 91.21; 536/24.3, 24.31, 24.32, 24.33

[56] References Cited

U.S. PATENT DOCUMENTS

| | | | |
|---|---|---|---|
| 5,200,314 | 4/1993 | Urdea | 435/6 |
| 5,273,882 | 12/1993 | Snitman et al. | 435/6 |
| 5,484,699 | 1/1996 | Bouma et al. | |

FOREIGN PATENT DOCUMENTS

| | | |
|---|---|---|
| 0362042 | 4/1990 | European Pat. Off. |
| 4503158 | 6/1992 | Japan |
| WO 9502068 | 1/1995 | WIPO |

OTHER PUBLICATIONS

Oka et al NAR vol. 22, No. 9 pp. 1541–1547, 1994.

*Primary Examiner*—Kenneth R. Horlick
*Assistant Examiner*—Jeffrey Siew
*Attorney, Agent, or Firm*—Birch, Stewart, Kolasch & Birch, LLP

[57] ABSTRACT

A method for concentrating a mutant nucleic acid. In particular, the present method is capable of selectively separating and collecting a mutant nucleic acid from a sample including both the nucleic acid and the mutant nucleic acid. Also, an assay kit for nucleic acid concentration.

15 Claims, No Drawings

METHOD AND NUCLEIC ACID-CONCENTRATIING ASSAY KIT FOR CONCENTRATING MUTANT NUCLEIC ACID

This application is the national phase under 35 U.S.C. §371 of prior PCT International Application No. PCT/JP 96/02617 which has an International filing date of Sep. 13, 1996 which designated the United States of America, the entire contents of which are hereby incorporated by reference.

TECHNICAL FIELD

The present invention relates to a method for concentrating a mutant nucleic acid which is capable of selectively separating and removing the normal nucleic acid, or selectively separating and collecting a mutant nucleic acid from a sample including both the nucleic acid wherein the particular segment of the nucleic acid comprises the normal gene and a minute amount of the mutant nucleic acid having a nucleotide sequence slightly different from the normal nucleic acid. The present invention also relates to an assay kit for nucleic acid concentration in order conduct said concentration method.

BACKGROUND TECHNOLOGY

Molecular biology and genetics have recently experienced tremendous progress, and the findings accumulated in these field contributed in the elucidation of biological phenomena in both chemical and physical senses and such findings also gave fundamental impacts on medical researches and practices. DNA medicine working from the level of DNA is rapidly expanding to the clinical fields at a rate far beyond our expectation. Today, DNA is considered to be associated in practically every disease, and diagnosis on the gene level has become indispensable.

It has also been revealed that substantially all of the various enzyme deficiencies which have been known as congenital dysbolism for quite some time are gene diseases, and detection of mutation in the nucleotide sequence of the gene is quite effective in the gene diagnosis of such diseases.

Gene diagnosis of the diseases induced by acquired dysbolism, for example, cancer have encountered with an extreme difficulty in collecting the cancer cell from the cancer lesion, and normal cells were always included in the collected specimen. Accordingly, there is a need for a method by which only the mutant gene in the cancer cell can be specifically detected under the conditions where both the normal cells and the cancer cells are present. In the current process, detection of the mutant gene is possible when the amount of the mutant gene is about one tenth of the normal gene, namely, when the amount of the cancer cells is about one fifth to one tenth of the normal cells. Detection of the mutant gene of smaller amount, however, has been difficult, and the gene diagnosis is not yet effectively utilized in the early stage detection and early stage treatment of cancer.

Recent development in gene amplification methods such as PCR (polymerase chain reaction) enabled increase of the amount of gene. Not only such mere increase in the amount of the gene but also increase in the percentage of the mutant gene in the sample is required for identifying cancer cell from normal cell, or mutation of the gene responsible for the particular genetic disease of a patient from the gene of a normal donor. In such a case, the particular gene can be selectively concentrated by subtraction method (In Current Protocol in Molecular Biology, (1992), John Wiley & Sons, Inc.) when the particular gene of either cell includes a deletion or an insertion of a considerable length or when the particular gene is expressed only in either cell.

Detection of the mutant gene by the subtraction method, however, was substantially difficult when the mutation of the gene responsible for the disease was minute, namely, when the size of the mutation through deletion, addition or substitution is very small, or when no substantial difference in the gene expression level is found between the genes.

SUMMARY OF THE INVENTION

The present invention has been made in view of the situation as described above, and an object of the present invention is to provide a nucleic acid concentration method which is capable of readily and reliably concentrating a mutant nucleic acid of a sample even if the sample contains both the normal nucleic acid wherein the particular segment of the target nucleic acid is normal and the mutant nucleic acid of minute amount, and which is capable of detecting the mutant nucleic acid of minute amount and identifying the mutant nucleic acid; as well as an assay kit for nucleic acid concentration to conduct the concentration process as described above.

In order to accomplish the object as described above, the inventors of the present invention made an extensive study on the method for selectively concentrating the mutant nucleic acid in a sample wherein the target nucleic acid comprises those wherein the particular segment thereof comprises the normal nucleic acid and those comprising the mutant nucleic acid. The inventors then found that normal nucleic acid can be selectively removed from the reaction solution and the mutant nucleic acid can be readily and reliably concentrated by using a nucleic acid sample prepared by amplifying the normal nucleic acid and the mutant nucleic acid in the sample, and a labeled nucleic acid standard comprising an amplification product of the normal nucleic acid having incorporated therein a label capable of binding to a solid support; adding to said nucleic acid sample an equimolar amount or more of the labeled nucleic acid standard and allowing the mixture to undergo thermal denaturation and competitive hybridization by using a very gentle temperature gradient; and separating and removing the hybridizate having said label capable of binding to the solid support from the reaction solution after the hybridization by trapping such hybridizate on the solid support. The present invention was accomplished on the bases of such a finding.

In other words, the present invention is an improvement and development of PCR-PHFA method (PCT/JP94/01106, Nucl. Acids. Rec. 22, 1541 (1994)), which is a method for determining identity of a nucleic acid proposed by the inventors of the present invention, and in the present invention, the PCR-PHFA method is utilized for the concentration of the mutant nucleic acid. The mutant nucleic acid is concentrated by utilizing the competitive hybridization of the PCR-PHFA method, namely, the nature that, when there is a difference as slight as 1 base difference between the normal nucleic acid and the mutant nucleic acid, the pair of strands having the completely complementary sequence will hybridize first.

The principle of the process is as described below. When a sample containing the normal nucleic acid and the nucleic acid of a minute amount having a slight mutation is amplified and used for the nucleic acid sample; and in the meanwhile, the normal nucleic acid is amplified with a label capable of binding to a solid support incorporated therein to use the amplified product for the labeled nucleic acid standard; and an equimolar amount or more of the labeled nucleic acid standard is added to said nucleic acid sample; and the mixture is allowed to undergo competitive hybridization by using an extremely gentle temperature gradient; the normal nucleic acid in the hybridization reaction solution will have a nucleotide sequence completely complementary to the nucleic acid strand (the nucleic acid strand obtained by amplification of the normal nucleic acid) of the labeled nucleic acid standard having the label capable of binding to the solid support incorporated therein, and will form a double strand nucleic acid with such strand. The single strand nucleic acid from the mutant nucleic acid will bind to the complementary strand from the mutant nucleic acid (having no label capable of binding to the solid support incorporated therein) rather than the synthesized nucleic acid strand having the label capable of binding to the solid support incorporated therein. Therefore, when the reaction solution is contacted with the solid support having a functionality which specifically binds to said label incorporated therein to promote adsorption, the double strand nucleic acids having the label capable of binding to the solid support will selectively bind to the solid support. When the fraction of the reaction solution which failed to bind to the solid support is collected, the nucleic acid present in the fraction collected will be the amplified product of the nucleic acid that had been present in the original sample from which the normal nucleic acid has been removed, and as a consequence, the mutant nucleic acid will be concentrated.

In the case as described above, even when the sample contains an extremely minute amount of the mutant nucleic acid, the mutant nucleic acid can be selectively concentrated to a detectable concentration in a reliable manner by repeating the series of concentration steps as described above, or the steps after the competitive hybridization for two or more times. Consequences of such process are not only the increase in the amount of the mutant nucleic acid but also the increase in the percentage of the mutant nucleic acid. A convenient and reliable detection of the mutant nucleic acid, and hence, identification of the mutant nucleic acid are thereby enabled. Elucidation of the genetic disease and development of treatments through analysis of the mutation is also enabled.

Furthermore, in identifying the cancer cell and the normal cell, or in detecting the mutation of the gene responsible for a particular genetic disease in the patient and the normal donor, this method is capable of concentrating the mutant gene which could not have been accomplished by the conventional subtraction method. More illustratively, this method reliably accomplishes selective concentration of the mutant gene to enable easy and reliable identification of the mutant gene even when the mutation in the gene responsible for the disease is minute, namely, when the extent of mutation by deletion, addition or substitution of the gene is very small, and no substantial difference is found in the level of the gene expression.

In addition, this method can be used for detecting a mutant nucleic acid from the abnormal cell of a minute amount in the sample containing both the normal cell and the abnormal cell, not only when the target nucleic acid comprises a double strand DNA but also when the target nucleic acid is single strand DNA, or single or double strand RNA, and the method can be widely adapted to detect not only the DNA mutation but also abnormality of mRNA (messenger DNA) in the cell and abnormality of the chromosomal DNA for the mRNA.

In accordance with the situation as described above, there is provided as a first aspect of the present invention, a method for selectively concentrating a mutant nucleic acid constituting a particular segment of a target nucleic acid wherein a cycle comprising the steps of (1) to (3):

(1) the step of preparing a nucleic acid sample by amplifying said particular segment of said target nucleic acid, (2) the step of adding to said nucleic acid sample an equimolar amount or more of a labeled nucleic acid standard prepared by incorporating a label capable of binding to a solid support into a nucleic acid having a nucleotide sequence complementary to the normal nucleic acid sequence of said particular segment of said target nucleic acid to promote competitive hybridization, and (3) the step of separating and removing the hybridizate having said label capable of binding to the solid support and the residual labeled nucleic acid standard in the reaction solution after the competitive hybridization by trapping them on the solid support is effected one or more times; or wherein said cycle is effected once and said steps (2) and (3) are repeated one or more times.

There is also provided an assay kit for concentration for conducing the above-described concentration method which is characterized in that said kit comprises nucleic acid sample-preparing reagents for preparing the nucleic acid sample by amplifying the particular segment of the target nucleic acid; the labeled nucleic acid standard prepared by incorporating a label capable of binding to a solid support into a nucleic acid having a nucleotide sequence complementary to the normal nucleic acid sequence of said particular segment of said target nucleic acid; and the solid support having a site capable of binding to said label.

In the course of further investigation, the inventors of the present invention found that, the mutant nucleic acid can be readily and reliably concentrated in a manner reverse to the method as described above. More illustratively, an amplified product of the normal nucleic acid and the mutant nucleic acid in the sample having incorporated therein two labels which are respectively capable of binding to solid supports is prepared and the amplified product is used for a labeled nucleic acid sample; a nucleic acid standard comprising an amplification product of the normal nucleic acid is prepared; to said labeled nucleic acid sample is added an equimolar amount or more of said nucleic acid standard and the mixture is allowed to undergo thermal denaturation and competitive hybridization by using a very gentle temperature gradient; and the hybridizates having one of said labels are trapped from the reaction solution after the hybridization by contacting the reaction solution with first solid support which selectively binds to said one label. The thus collected hybridizates are contacted with the second solid support which selectively binds to the second label to trap the hybridizate having the second label to thereby collect the hybridizate having both labels; or alternatively, the hybridizates collected on the first solid support are denatured into single strand nucleic acids, and the single strand nucleic acids are contacted with the second solid support to collect the single strand nucleic acid having only the second label. The mutant nucleic acid is thereby selectively collected, enabling convenient, reliable concentration of the mutant nucleic acid.

In other words, when a sample containing both the normal nucleic acid and the nucleic acid of a minute amount having a slight mutation is amplified with two types of labels respectively capable of binding to solid supports incorporated therein to use the amplified product for the labeled nucleic acid sample; the normal nucleic acid is amplified to use the amplified product for the nucleic acid standard; an equimolar amount or more of said nucleic acid standard is added to said labeled nucleic acid sample; and the mixture is allowed to undergo competitive hybridization by using an extremely gentle temperature gradient; the labeled nucleic acid strand of said normal nucleic acid in the hybridization reaction solution will have a nucleotide sequence completely complementary to the nucleic acid strand (the nucleic acid strand obtained by amplification of the normal nucleic acid) of the nucleic acid standard, and will form a double strand nucleic acid with such strand. Therefore, under such conditions, the single strand nucleic acid from the mutant nucleic acid will bind to the complementary strand from the original mutant nucleic acid (the nucleic acid strand having the label capable of binding to the solid support incorporated therein) rather than the nucleic acid strand from said nucleic acid standard. Accordingly, the normal nucleic acid of the labeled nucleic acid sample and the unlabeled nucleic acid standard will experience swapping of their complementary strands and the hybridizate formed will only have either one of the labels, whereas the mutant nucleic acid of the labeled nucleic acid sample will not experience any swapping of the complementary strands with the nucleic acid standard remaining as the original double strand nucleic acid having the two types of labels, and the remaining nucleic acid standard will comprise the original unlabeled double strand nucleic acid. When the hybridizates having the first label are collected by using the first solid support which selectively binds to said first label, and the hybridizate having the second label is collected from the hybridizates collected on the first solid support by using the second solid support having the second label, the hybridizate having both types of the labels, namely, the mutant nucleic acid which did not undergo swapping of the complementary strands with the nucleic acid standard in the course of the competitive hybridization is selectively recovered to enable the concentration of the mutant nucleic acid. It should be noted that, in the course of the separation and collection from the first solid support of the hybridizates collected by the first solid support, the double strand hybridizates may be denatured for separation and collection of the single strand nucleic acid which is not involved in the binding onto the solid support, and the thus collected single strand nucleic acid may be contacted with said second solid support to collect the single strand nucleic acid derived from the hybridizate having both types of the labels. The thus concentrated mutant type target nucleic acid in the form of a single strand nucleic acid may then be amplified by using primers or the like to thereby obtain double strand nucleic acid.

In the case as described above for the second method, when the sample contains an extremely minute amount of the mutant nucleic acid, the mutant nucleic acid can be selectively concentrated to a detectable concentration in a reliable manner by repeating the series of concentration steps as described above, or the steps after the competitive hybridization for two or more times. According to this method, such selective, reliable concentration is also enabled even when the extent of mutation by deletion, addition or substitution of the gene is very small, and no substantial difference is found in the level of the gene expression. In addition, this method can be used not only when the target nucleic acid comprises a double strand DNA but also when the target nucleic acid comprises a single strand DNA, or single or double strand RNA, and the method can be widely adapted to detect not only the DNA mutation but also abnormality of mRNA (messenger DNA) in the cell and abnormality of the chromosomal DNA for the mRNA.

In accordance with the situation as described above, there is provided as a second aspect of the present invention, a method for selectively concentrating a mutant nucleic acid constituting a particular segment of a target nucleic acid wherein a cycle comprising the steps of (1') to (4'):

(1') the step of preparing a labeled nucleic acid sample by amplifying said particular segment of said target nucleic acid, and simultaneously, incorporating two types of labels respectively capable of binding to solid supports into the amplification product, (2') the step of adding to said labeled nucleic acid sample an equimolar amount or more of a nucleic acid standard having a nucleotide sequence complementary to the normal nucleic acid sequence of said particular segment of said target nucleic acid to promote competitive hybridization, (3') the step of collecting the hybridizates having one of said two types of labels from the reaction solution after the competitive hybridization by trapping such hybridizates on the first solid support which selectively binds to said one label, and (4') the step of collecting the hybridizate having both of said two types of labels or a single strand nucleic acid derived from said hybridizate by contacting the hybridizates collected in the step (3') with the second solid support which selectively binds to the other label is effected one or more times; or wherein said cycle is effected once and said steps (2') to (4') are repeated one or more times.

There is also provided an assay kit for conducing the above-described second concentration method, and this assay kit for the concentration of the mutant nucleic acid is characterized in that this kit comprises:

labeled nucleic acid sample-preparing reagents for preparing the labeled nucleic acid sample by amplifying the particular segment of the target nucleic acid simultaneously with incorporation of two types of labels into the amplified product;

nucleic acid standard having a nucleotide sequence complementary to the normal nucleic acid sequence of said particular segment of the target nucleic acid;

first solid support having a site capable of binding to one label; and second solid support having a site capable of binding to the other label.

It should be noted that, in the above-described first and second concentration methods, and the assay kits for conducing such methods, "a nucleic acid having a nucleotide sequence complementary to the normal nucleic acid sequence of said particular segment of said target nucleic acid" in said nucleic acid standard when the target nucleic acid comprises a double strand DNA, may be either a single strand nucleic acid having a nucleotide sequence complementary to the normal nucleotide sequence of one nucleic acid strand of said double strand DNA, or a double strand nucleic acid comprising a pair of nucleic acid strands which are respectively complementary to the normal nucleotide sequence of one nucleic acid strands of said double strand DNA.

BEST MODE FOR CARRYING OUT THE INVENTION

Next, the present invention is described in detail.

As described in the foregoing, the method for concentrating a mutant nucleic acid of the present invention is the method wherein the mutant nucleic acid in the particular segment of the target nucleic acid is selectively concentrated, and the above-described first method comprises (1) the step of preparing a nucleic acid sample by amplifying said particular segment of said target nucleic acid, (2) the step of competitive hybridization of said nucleic acid sample with the labeled nucleic acid standard, and (3) the step of separating and removing the competitive hybridization product derived from the normal nucleic acid and the remaining labeled nucleic acid standard from the reaction solution after the competitive hybridization by utilizing the label.

The target nucleic acid in said step (1) is typically obtained from a specimen collected from a living organism, and typical specimens include blood, tissue section, and excreta such as feces and urine from human. In the case of prenatal diagnosis, the specimen may comprise cells of the fetus in the amniotic fluid and cells of cleaved ovule in the test tube. The specimens may be preliminarily subjected to cytolysis by treating the specimen using an enzyme, heat or a surfactant, ultrasonication, or a combination thereof directly or after optional concentration by precipitation through a procedure like centrifugation. Such cytolysis is effected for the purpose of exposing the DNA or the RNA from the target tissue. In practice, the cytolysis may be carried out in accordance with a known procedure such as the one described in PCR PROTOCOLS, Academic Press Inc., p14, p352 (1990) or other documents. The specimen may preferably contain the DNA or the RNA in a total amount of 1 to 100 $\mu$g although the DNA or the RNA in an amount of less than 1 $\mu$g is well amplifiable. The resulting DNA is cut with an appropriate restriction enzyme to obtain the DNA fragment of the particular segment having the ends of predetermined types. When the target nucleic acid is a mRNA, the mRNA is transcribed into a cDNA (complementary DNA) with a reverse transcriptase, and the cDNA is cut with the appropriate restriction enzyme.

Next, the above-described DNA fragment is subjected to gene amplification using primers having no label capable of binding to the solid support incorporated therein to thereby prepare the nucleic acid sample. In this case, the template used may comprise the above-described DNA fragment having linkers respectively having a nucleotide sequence complementary to the nucleotide sequence of the primers linked to its opposite ends. The primers are not limited to any particular type, and any oligonucleotides generally used in the gene amplification may be used. Exemplary such primers are the oligonucleotides having an amino alkyl group incorporated on their 5' end.

The labeled nucleic acid standard used in said step (2) may be prepared by amplifying a template derived from the normal cell or a confirmed DNA sample using the primers each comprising a primer main segment having the nucleotide sequence the same as those used in the above-described step (1) having the label capable of binding to the solid support incorporated therein. In such a case, the position of the label in said primers is not limited to any particular position as long as the label does not markedly interfere with the efficiency of the primer extension reaction. The preferable positions of the label, however, are the part of the hydroxyl group near the 5' end, the part of the base, or the part of the active group in the phosphate diester, and the label capable of binding to the solid support may be selected depending on the nature of the solid support or the nature of the substance modifying the solid support.

In this case, the label is incorporated into the oligonucleotide of the primers for the purpose of separating and removing the unnecessary DNA in said step (3) by binding of the unnecessary DNA onto the solid support, and exemplary combination of the label and the substance on the solid support which is capable of binding to the label include, biotin and streptavidin or avidin; a hapten and an antibody, a ligand and a receptor, a particular nucleic acid and a DNA-binding protein which binds to such nucleic acid. Among these, the one having higher heat stability and smaller molecular size is used on the side of the oligonucleotide. For example, in the case of biotin and streptavidin, it is preferable to use the biotin for the label of the oligonucleotide and bond the streptavidin to the solid support, and the oligonucleotide will then bind to the solid support through the binding of the biotin to the streptavidin. Exemplary haptens include compounds having 2,4-dinitrophenyl group and digoxigenin, and the above-mentioned biotin and fluorescent substances such as phenylthioisocyanate can also be used as a hapten. The label such as biotin, the hapten, or the ligand as described above may be incorporated either alone or in combination of two or more by a known procedure (see Japanese Patent Application Laid-Open Nos. 59-93099, 59-148798, and 59-204200). The solid support may typically comprise a well or magnet beads having a site capable of binding to the above-described label, and in the latter case, the magnet beads may be introduced into the reaction solution for the binding with the nucleic acid, and then recovered from the reaction solution by using a magnet.

When the specimen is amplified with the primers having no label capable of binding to the solid support and when the labeled nucleic acid standard is prepared by amplification using the primers having the label capable of binding to the solid support, gene amplification reaction based on the extension of the primers will take place, and the gene amplification process utilized may typically be a known process such as PCR (Polymerase Chain Reaction), LCR (Ligase Chain Reaction), 3SR (Self-sustained Sequence Replication), SDA (Strand Displacement Amplification), or the like (Manak, DNA Probes, 2nd Edition, p 255–291, Stockton Press (1993)), and the most preferred is PCR.

In such case, the primer extension is promoted by allowing 4 types of nucleotide triphosphates [deoxy adenosine triphosphate (dATP), deoxy guanosine triphosphate (dGTP), deoxy cytidine triphosphate (dCTP), and deoxy thymidine triphosphate (dTTP), the mixture of which is often called dNTP] to be incorporated into the primer as the substrates.

In the extension of the nucleic acid, amplification reagents including the nucleotide triphosphates as described above and nucleic acid extending enzyme are employed. The nucleic acid extending enzyme may comprise any DNA polymerase such as $E.$ $coli$ DNA polymerase I, Klenow fragment of $E.$ $coli$ DNA polymerase I, T4 DNA polymerase, or the like. The most preferred are thermally stable DNA polymerases such as Taq DNA polymerase, Tth DNA polymerase, Vent DNA polymerase, and the like, and use of such thermally stable DNA polymerase enables automatic repetition of the amplification cycle with no need of supplementing the fresh enzyme in each cycle as well as use of an annealing temperature in the range of from 50 to 60° C. to realize an improved specificity in the recognition of the target sequence by the primer. A rapid gene amplification of high specificity is thereby realized. (For further detail, see Japanese Patent Application Laid-Open Nos. 1-314965 and 1-252300.)

In this reaction, an oil may be added to the reaction solution for the purpose of preventing evaporation of the moisture content. Any oil can be used as long as the oil separates from the water and has a specific gravity lower than the water, and typical oils include silicone oil, mineral oil, and the like. Such oil is unnecessary in some gene amplification apparatus, and the primer extension reaction may also be carried out in such an apparatus.

By repeating the extension reaction using the nucleic acid amplification primers as described above, the nucleic acids can be amplified at a high efficiency to enable the production of the nucleic acid sample and the labeled nucleic acid standard. It should be noted that the specific conditions and the like for the gene amplification may be determined in accordance with the known methods described in various references such as Jikken Igaku (Experimental Medicine), Yodosha, 8, No. 9 (1990), PCR Technology, Stockton Press (1989).

In producing the nucleic acid sample, the thus amplified DNA may be mass-produced in a host/vector system, namely, by incorporating the DNA in a vector selected from plasmid vectors, phage vectors and chimeric vectors derived from a plasmid and a phage and introducing the vector in a propagatable host such as a bacteria such as *Escherichia coli* and *Bacillus subtilis,* and Yeast (*Saccharomyces cerevisiae*) (gene cloning).

Instead of the gene amplification, the labeled nucleic acid standard may be prepared by enzymatically cleaving a natural gene by using restriction enzymes. The labeled nucleic acid standard may also be prepared by amplifying the normal nucleic acid, and then subjecting to the gene cloning as in the case of the nucleic acid sample as described above. In some cases, the labeled nucleic acid standard may be produced by chemical synthesis. Typical chemical synthesis processes are triester method and phosphite method, and the labeled nucleic acid standard may be produced by mass-producing the single strand DNA in an automatic synthesizer by using liquid phase method or solid phase synthesis method using an insoluble support, and annealing the single strand DNA to produce the double strand DNA.

It should be noted that, in the present invention, the target nucleic acid is not necessarily a DNA, and may be an RNA. In such a case, the RNA may be tRNA (transfer RNA), mRNA (messenger RNA) or rRNA (ribosomal RNA). The RNA, however, may preferably be a mRNA which reads and transduces the genetic information of the DNA. When the target gene is a mRNA which is free from introns and solely comprises exons (coding region of the genetic information), the detection and identification of its mutation is quite meaningful since the mutation found is the abnormality directly expressing the genetic information. 100% full estimation of the characteristics expressed by the DNA is not always possible in spite of the fact that the basic design of the gene is determined by the DNA. One gene (one transcription product pre-mRNA) may undergo an alternative splicing to produce a plurality of mRNA (i.e. a plurality of proteins), or alternatively, a pre-mRNA may experience a phenomenon (RNA editing) wherein some nucleotides are inserted or removed in the course of from the pre-mRNA to the mRNA. Therefore, it is the analysis of the mRNA and not the DNA that is necessary for the investigation of the mutation in the regulatory gene and promoter region or tissue-specific expression. The concentration method of the present invention wherein the mutant mRNA is effectively concentrated by using the mRNA for the target nucleic acid greatly contributes for the analysis of the mRNA. It should be noted that when the target nucleic acid comprises a mRNA, the mRNA may be directly amplified to use the amplified product for the nucleic acid sample. However, it is generally preferable to first transcribe the mRNA into a cDNA by using a reverse transcriptase and then amplify the cDNA by PCR (RT-PCR), so that the resulting amplified DNA may be used for the nucleic acid sample.

Furthermore, in the present invention, either one of the nucleic acid sample and the labeled nucleic acid standard may comprise a single strand DNA or a single strand RNA. In such case, the single strand RNA may be prepared by chemical synthesis, or alternatively, by in vitro transcription using an RNA polymerase of a phage such as SP6 or T7. The single strand DNA may also be prepared by chemical synthesis, or alternatively, by cloning wherein the DNA is incorporated in a phage DNA such as M13 phage or a phage plasmid DNA capable of producing the single strand DNA.

When an RNA is used for the labeled nucleic acid standard, or when the DNA is amplified by a method other than those using the primers, the label capable of binding to the solid support may comprise the label as described above, and such label may be introduced either chemically or enzymatically by means of a known method (see Japanese Patent Application Laid-Open Nos. 1-252300 and 1-63393).

After the gene amplification as described above, the competitive hybridization is allowed to take place by using the DNA or the RNA prepared from the target nucleic acid having no label capable of binding to the solid support for the nucleic acid sample, and the DNA or the RNA prepared from the sample having the label capable of binding to the solid support for the labeled nucleic acid standard, and adding to the nucleic acid sample an equimolar amount or more of the labeled nucleic acid standard.

In such a case, it is ideal that the labeled nucleic acid standard as described above comprises a double strand DNA having opposite ends whose nucleotide sequence is identical with the nucleic acid sample as described above. The nucleotide sequence of opposite ends may not necessarily be completely the same, and a satisfactory concentration may be accomplished when the differences in length on opposite ends between the strands of the nucleic acid sample and the labeled nucleic acid standard are respectively within about 10 bases. It should be noted that, when either the nucleic acid sample or the labeled nucleic acid standard comprises a single strand DNA or a single strand RNA, there is no particular limit in the strand length difference between the nucleic acid sample and the labeled nucleic acid standard.

In the present method for concentrating the mutant nucleic acid, the competitive hybridization between the nucleic acid sample and the labeled nucleic acid standard may be one of the following three combinations: DNA—DNA hybridization, DNA-RNA hybridization, and RNA—RNA hybridization depending on the identity of the target nucleic acid whether it is a DNA or an RNA, and the mutant DNA or the mutant RNA can be effectively concentrated irrespective of the type of the hybridization. In particular, when the target nucleic acid is an RNA, the concentration method is particularly useful in detecting the particular mRNA in the cell and in detecting the chromosomal DNA for the mRNA as described in the foregoing.

In the course of the competitive hybridization, the nucleic acid sample and the labeled nucleic acid standard should be denatured in the first place, and the denaturation is preferably accomplished by thermal or alkaline denaturation. The nucleic acids may be mixed either immediately before the denaturation or after the denaturation. In the present invention, an equimolar amount or more of the labeled nucleic acid standard should be added to the nucleic acid sample, and it is generally preferable to add the labeled nucleic acid standard in a molar amount about 10 to 50 times in excess of the nucleic acid sample. The optimal conditions, however, may differ by the length of the nucleic acid, the nucleotide sequence, and the extent of the mutation.

In the competitive hybridization, the composition of the solution, and particularly, salt concentration should be adjusted for optimization depending on the length of the nucleic acid. In the hybridization, SSC (20×SSC: 3 M sodium chloride, 0.3 N sodium citrate) and SSPE (20×SSPE: 3.6 M sodium chloride, 0.2 M sodium phosphate, 2 mM EDTA) are generally used for the salt concentration adjustment, and such solution can also be used in the concentration method of the present invention after diluting to an appropriate concentration after optional supplementation with an organic solvent such as dimethylsulfoxide (DMSO) and dimethylformamide (DMF).

The competitive hybridization may be accomplished by adding an equimolar amount or more of the labeled nucleic acid standard to the nucleic acid sample that has been denatured as described above, and gradually reducing the temperature from a high temperature. The temperature conditions of this step is adequately optimized according to the length and sequence of the nucleic acid to be hybridized and the type and extent of the mutation between the nucleic acid sample and the labeled nucleic acid standard. The temperature conditions, however, are generally such that the temperature is reduced from 98° C. to 58° C. at a rate of 1° C. per 3 to 10 minutes, and more preferably, such that the temperature is reduced from 98° C. to 70° C. at a rate of 1° C. per 10 minutes.

Next, the product of the competitive hybridization is separated and removed by trapping the residual labeled nucleic acid standard and the nucleic acid sample that had hybridized to the labeled nucleic acid standard on the solid support by means of the label capable of binding to the solid support present on the labeled nucleic acid standard, namely, by the binding of the label to the solid support. It should be noted that the procedure as described above is repeated one or more times, and preferably three or more times, and the residual labeled nucleic acid standard and the nucleic acid sample that had hybridized to the labeled nucleic acid standard will then reliably bond on the solid support to enable the separation and the removal.

When the label capable of binding to the solid support present on the labeled nucleic acid standard is biotin, and the solid support is a well of a microtiter plate having streptavidin immobilized thereto, the product of the competitive hybridization may be added to the well, and the reaction may be allowed to take place at 25° C. or room temperature for 15 to 30 minutes under shaking. The reaction conditions, however, may vary depending on the type of the label and the solid support employed.

As a consequence of the procedure as described above, the fraction which did not bind to the solid support, namely the residual reaction solution contains the nucleic acid which did not hybridize with the labeled nucleic acid standard, namely the nucleic acid having a nucleotide sequence different from the labeled nucleic acid standard at a content higher than the original specimen. When the content of the mutant nucleic acid in the original specimen is extremely minute, and the content of the mutant nucleic acid after one cycle of the concentration process as described above may be below the detection level, the concentration process may be repeated two or more times to increase the concentration of the mutant nucleic acid in stepwise. The mutant nucleic acid is then reliably concentrated to a detectable concentration. In such a case, the absolute amount of the mutant acid concentrated can be increased if the concentration procedure is fully repeated from the step of amplifying the target nucleic acid in the concentration after the second cycle. Such full repetition of all steps, however, is not always necessary, and the degree of the concentration can be increased by merely repeating the steps after the competitive hybridization.

Next, the concentration method according to second aspect of the present invention is the method comprising the steps of (1') preparing a labeled nucleic acid sample having incorporated therein two types of labels, (2') allowing said labeled nucleic acid sample and a nucleic acid standard to undergo competitive hybridization, (3') collecting the hybridizates having one of said two types of labels from the reaction solution after the competitive hybridization, and (4') collecting the hybridizate having both of said two types of labels or a single strand nucleic acid derived from said hybridizate from the hybridizate collected to thereby selectively recover the mutant nucleic acid. In other words, the mutant nucleic acid is concentrated in this second method in a way reverse to the above-described first method by allowing said labeled nucleic acid sample and a nucleic acid standard to undergo competitive hybridization, and separating and collecting the mutant nucleic acid in the nucleic acid sample by utilizing the two types of the labels.

In said step (1') of preparing the labeled nucleic acid sample, the labeled nucleic acid sample may be prepared by amplifying the target nucleic acid obtained from the specimen in a manner similar to the first method as described above, and in the second method, two types of labels are incorporated in the nucleic acid sample to prepare the labeled nucleic acid sample. The label incorporation process is similar to the preparation of the labeled nucleic acid standard in the first method, and more illustratively, the target nucleic acid is preferably amplified by PCR using the primers having the labels incorporated therein. In the case of the second method, two different types of labels are incorporated into the two primers to prepare two types of primers each having the label different from the other primer, and the thus prepared two primers are used in the amplification of the target nucleic acid to prepare the labeled nucleic acid sample having the two different labels incorporated therein. It should be noted that the pretreatment of the target nucleic acid, the conditions in the PCR amplification, and the like are as in the case of the first method.

The two types of labels incorporated in the labeled nucleic acid sample as described above may be any labels as long as they are different from each other, and the label the same as the one incorporated in the labeled nucleic acid sample in the first method may be used. Preferable labels are those having high binding specificity to the binding site, and exemplary preferable combination is biotin and hapten.

As in the case of the first concentration method, the labeled nucleic acid sample may be prepared without using primers, namely, by amplifying in host/vector systems selected from plasmid vectors, phage vectors, and chimeric vectors prepared from a plasmid and a phage. In such a case, the two labels may be incorporated either chemically or enzymatically after the amplification of the target nucleic acid by any known method.

The nucleic acid standard used in the step (2') may be prepared in the process the same as the first method except that no label is incorporated, and the competitive hybridization between the labeled nucleic acid sample and the nucleic acid standard may be carried out as in the competitive hybridization of the first method.

In the second method, the mutant nucleic acid is selectively separated and collected from the reaction solution by the steps (3') and (4'). More illustratively, the reaction solution after the hybridization is contacted with the first solid support which selectively binds to one of the two labels to collect the hybridizates having at least said first label. The hybridizates collected by this procedure include the hybridizate having the first label which is produced by the hybridization between the nucleic acid standard and the normal nucleic acid of the labeled nucleic acid sample, and the mutant nucleic acid having both of the two labels comprising the original two strands which did not hybridize with the nucleic acid standard. The thus collected hybridizates are contacted with the second solid support which selectively bind to the other one of the two labels to collect the hybridizate having the other label. Of the hybridizates with one label collected by the first solid support, the hybridizate collected by this procedure for separation and recovery is the one which also has the other label, namely, the mutant nucleic acid having both labels, and the mutant nucleic acid is thereby concentrated.

In this method, the first and second solid supports may be respectively prepared as in the case of the first method, and the binding site for the label may be adequately selected to enable selective binding with the label depending on the two types of labels incorporated in the labeled nucleic acid sample. The binding sites may be the same as those described in the first method. For example, when biotin and a hapten are used for the two labels, streptavidin or avidin is used for selective binding with biotin, and an anti-hapten antibody is used for selective binding with the hapten. The hybridizates trapped by the solid support may be separated and recovered from the solid support according to an appropriate known method depending on the type of the labels and the binding sites of the solid supports. The hybridizates trapped by the first solid support is generally separated and recovered from the solid support in the form of a double strand nucleic acid and contacted with the second solid support. The double strand nucleic acid, however, may be separated for separation and recovery of the single strand nucleic acid which is not involved in the binding to the solid support, and the thus recovered single strand nucleic acid may be brought in contact with the second solid support, for example, when the concentration is effected merely for the purpose of detecting the nucleic acid. In such a case, the mutant nucleic acid is concentrated in the form of a single strand nucleic acid. The single strand nucleic acid, however, may be readily turned into the double strand nucleic acid by amplification using primers or the like. Furthermore, when the mutant nucleic acid is concentrated in the form of a single strand nucleic acid, magnet beads having incorporated therein a site capable of binding to the second label is preferably used for the second solid support, and the magnet beads may be recovered from the reaction solution by using a magnet.

In the second concentration method, the procedures other than those described in the foregoing may be carried out as in the case of the first method. The degree of concentration can also be increased in this second method by repeating the series of steps or the steps after the competitive hybridization.

Both of the methods for concentrating a mutant nucleic acid of the present invention have enabled to readily and reliably detect the mutant nucleic acid of a minute amount of the level which had been difficult to detect by detecting the mutant acid from the resulting concentrated solution. Furthermore, by increasing the content of the mutant nucleic acid, isolation of the mutant acid can be more readily accomplished to enable a convenient analysis of the structure and function of the mutant nucleic acid. More illustratively, gene structure such as nucleotide base sequence may be physically analyzed to realize gene therapy by gene manipulation and analysis of the genetic disease.

Detection of the mutant nucleic acid from the concentrated solution in the concentration method of the present invention may be accomplished by a known method. Exemplary preferable methods include detection by polyacrylamide gel electrophoresis and detection by using a probe labeled with a detectable label. In such a case, the detectable label may comprise either a nonradioactive label or a radioactive label, and use of a nonradioactive label is preferred. Exemplary nonradioactive substances which may be used for the label include substances which may be used as a direct label such as fluorescent substances [such as fluorescein derivatives (fluorescein isothiocyanate etc.), rhodamine and its derivatives (tetramethylrhodamine isothiocyanate etc.)], chemiluminescent substances (such as acridine), and substances showing delayed fluorescence (DTTA, manufactured by Pharmacia).

A known mutant nucleic acid prepared by intentional mutagenesis in a particular nucleic acid is sometimes required in the course of elucidating the functions of a particular gene or the functions and the like of the proteins translated from such gene. By using the concentration method of the present invention, the mutant nucleic acid can be selectively concentrated after the mutagenesis in the particular nucleic acid, and the mutant nucleic acid can be prepared at a high efficiency. More illustratively, after the intentional mutagenesis of the particular nucleic acid with a mutagen such as sulfurous acid, the mutant nucleic acid can be selectively concentrated and recovered by repeating the concentration process of the present invention by using the particular nucleic acid in the mixture for the target nucleic acid and preparing the labeled or unlabeled nucleic acid standard from the nucleic acid before the mutagenesis. The mutant nucleic acid is thereby prepared at a high efficiency.

Next, the assay kit for nucleic acid concentration of the present invention is an assay for readily and reliably concentrating the mutant nucleic acid by the mutant nucleic acid concentration method of the present invention. The kit for conducting the first concentration method as described above comprises reagents for preparing the nucleic acid sample by amplifying the particular segment of the target nucleic acid; labeled nucleic acid standard prepared by incorporating a label capable of binding to a solid support into a nucleic acid having a nucleotide sequence complementary to the normal nucleic acid sequence of said particular segment of said target nucleic acid; and the solid support having a site capable of binding to said label.

This assay kit is used in accordance with the first concentration method as described above, by preparing the nucleic acid sample by amplifying the target nucleic acid using said nucleic acid sample-amplifying reagents, said target nucleic acid being the one obtained from a specimen pretreated by cytolysis or the like, or a custom synthesized nucleic acid; adding the labeled nucleic acid standard having the label capable of binding to the solid support to said nucleic acid sample to allow the competitive hybridization to take place; and trapping the resulting hybridizate on the solid support to thereby separate and remove the strands which hybridized with the labeled nucleic acid standard.

The nucleic acid sample-amplifying reagents used for the preparation of the nucleic acid sample may comprise the unlabeled primers, phage DNA, phage plasmid DNA, or RNA polymerase in the case of the RNA preparation as described in relation to the first concentration method. It is, however, the primers as described above, that is most typically used for the nucleic acid sample-amplifying reagents. The reagents used in the amplification and hybridization of the nucleic acid, and the solid support may comprise those known in the art, and more illustratively, those described in the foregoing description of the concentration method of the present invention. A reagent for cytolysis used in the pretreatment of the specimen, an oil for preventing evaporation of the moisture content of the reaction solution, and the washing solution for washing of the nucleic acid and the like which failed to bind to the solid support as described above in relation to the concentration method of the present invention may also be used, and these components may be also incorporated in the assay kit for nucleic acid concentration of the present invention.

The labeled nucleic acid standard may comprise a labeled DNA prepared by the concentration method of the present invention. Instead of the labeled nucleic acid standard, the assay kit for concentration of the present invention may comprise labeled nucleic acid standard-amplifying reagents for preparing the labeled nucleic acid standard, and the labeled nucleic acid standard-amplifying reagents may include the primers comprising the primers capable of amplifying the particular segment of the target nucleic acid having incorporated therein the label capable of binding to the solid support. In such a case, the labeled nucleic acid standard is prepared before each concentration by using the labeled nucleic acid standard-amplifying reagents in accordance with the method described for the concentration method.

The kit for conducting the second concentration method comprises reagents for preparing the labeled nucleic acid sample by amplifying the particular segment of the target nucleic acid simultaneously with incorporation of two types of labels into the amplified product; nucleic acid standard having a nucleotide sequence complementary to the normal nucleic acid sequence of said particular segment of the target nucleic acid; first solid support having a site capable of binding to one of said two types of labels; and second solid support having a site capable of binding to the other one of said two types of labels.

This assay kit is used in accordance with the second concentration method as described above, by preparing the labeled nucleic acid sample labeled with two types of labels by amplifying the target nucleic acid using said labeled nucleic acid sample-amplifying reagents, said target nucleic acid being the one obtained from a specimen pretreated by cytolysis or the like, or a custom synthesized nucleic acid; adding the nucleic acid standard to said labeled nucleic acid sample to allow the competitive hybridization to take place; and sequentially trapping the resulting hybridizates on the first and second solid supports to thereby separate and recover the hybridizate having both labels which did not hybridize with the nucleic acid standard.

The labeled nucleic acid sample-amplifying reagents used for the preparation of the nucleic acid sample may comprise the two primers respectively labeled with a different label, phage DNA, phage plasmid DNA, or RNA polymerase in the case of the RNA preparation as described above in relation to the second concentration method. It is, however, the two primers as described above, that are most preferably used for the labeled nucleic acid sample-amplifying reagents. The reagents used in the amplification and hybridization of the nucleic acid, and the solid support may comprise those known in the art, and more illustratively, those described in the foregoing description of the concentration method of the present invention. A reagent for cytolysis used in the pretreatment of the specimen, an oil for preventing evaporation of the moisture content of the reaction solution, and the washing solution for washing of the nucleic acid and the like which failed to bind to the solid support as described above for the concentration method of the present invention may also be used, and these components may be also incorporated in the assay kit for nucleic acid concentration of the present invention.

The nucleic acid standard may comprise an unlabeled DNA having no label prepared by the concentration method of the present invention. Instead of the nucleic acid standard, the assay kit for concentration of the present invention may comprise nucleic acid standard-amplifying reagents for preparing the nucleic acid standard, and the nucleic acid standard-amplifying reagents may include the primers capable of amplifying the particular segment of the target nucleic acid. In such a case, the nucleic acid standard is prepared before each concentration by using the nucleic acid standard-amplifying reagents in accordance with the method described for the concentration method.

As described above, the method for concentrating mutant nucleic acid of the present invention is capable of selectively separating and removing, or selectively separating and recovering the mutant nucleic acid from the sample including both the nucleic acid wherein the particular segment of the nucleic acid comprise the normal gene and the mutant nucleic acid having a nucleotide sequence slightly different from the normal gene. The mutant nucleic acid of minute amount in the sample can be thereby readily and reliably detected to enable identification of the detected mutant nucleic acid. It is also possible to artificially induce a mutation in a particular gene, and selectively concentrate the mutant gene. In this way, the mutant nucleic acid can be efficiently prepared.

According to the present invention, candidate gene for a genetic disease or a cancer can be efficiently concentrated when the gene responsible for such genetic disease or cancer is unknown. In such a case, the nucleic acid standard may be prepared from the chromosomal DNA or mRNA from a normal donor or tissue, and the nucleic acid sample may be prepared from the chromosomal DNA or mRNA from a patient suffering from the disease or cancer tissue. The nucleic acid standard and the nucleic acid sample are amplified directly in the case of the chromosomal DNA, and after the reverse transcription into the double strand DNA in the case of the mRNA, by cleaving the DNA with an appropriate restriction enzyme, adding linkers, and conducting the concentration in accordance with the method of the present invention by using the primers complementary to the linker sequences. The group of genes whose nucleotide sequence is different between the normal donor or the tissue and the patient suffering from the disease or the cancer tissue is thereby selectively obtained.

The assay kit for concentration of the present invention is capable of selectively concentrating the mutant nucleic acid to enable detection and identification of the mutant nucleic acid when the kit is used in accordance with the method for concentrating a mutant nucleic acid of the present invention.

Therefore, the nucleic acid of a sufficient amount can be reliably prepared by the present invention, and the thus obtained mutant nucleic acid can be used in the analysis of its structure and function. Such analysis would greatly contribute for the elucidation of genetic diseases and gene therapies.

The present invention is described in further detail by referring to the Examples which by no means limit the scope of the present invention.

EXAMPLE 1

A process for selectively concentrating a mutant gene of human c-H-ras gene from a specimen including both the normal gene and the mutant gene is described.

The normal gene used was human c-H-ras gene, and the mutant gene used was the human c-H-ras gene wherein GGC (Gly) of the 12th codon has been substituted with GTC (Val).

Gene Amplification

Amplification of the DNA by PCR was conducted by using 1 ng of pSK-2 (a plasmid containing the normal gene) or pKY-1 (a plasmid containing the mutant gene) as described below for the template and 100 ng each of $NH_2$-PHR-1 and $NH_2$-CHRAS-1 as described below for the primers in the presence of 200 μM each of dATP, dGTP, dCTP, and dTTP in a solution containing 100 μl of Tris-HCl buffer (pH 8.8), 16.6 mM $(NH_2)_2SO_4$, 6.7 mM $MgCl_2$, 10 mM 2-mercaptoethanol and 2 units of Tth DNA polymerase.

The reaction was performed by heating the mixture at 94° C. for 10 minutes, and repeating 30 cycles of 30 sec. at 94° C., 30 sec. at 60° C., and 60 sec. at 72° C. The reaction solution was electrophoresed on agarose gel to confirm the size of the amplified product and the amplification rate.

$NH_2$-PHR-1

$NH_2$-5'ATGACGGAATATAAGCTGGTG3'    (SEQ ID NO: 1)

$NH_2$-CHRAS-1

$NH_2$-5'CTGGATGGTCAGCGCACTCTT3+    (SEQ ID NO: 2)

pSK-2

The plasmid having normal ras gene (T. Sekiya, Gann, 74, 794 (1983), available from JCRB (Japan Cancer Research Resources Bank).

pKY-1

The plasmid having mutation at 12th codon (M. H. Kraus and Y. Yuasa, Nature, 303, 775 (1983), available from JCRB (Japan Cancer Research Resources Bank).

Preparation of Test Sample

Next, the amplification product of the normal gene and the amplification product of the mutant gene were mixed at the ratio shown in Table 1 to prepare the samples having the mutant gene/normal gene ratios of 0%, 10%, 50% and 100%. The samples were diluted 1000 times with distilled water to prepare the test samples.

TABLE 1

| % of mutant gene | Amplified product from normal gene | Amplified product from mutant gene |
|---|---|---|
| 0% | 100 μl | 0 μl |
| 10% | 90 μl | 10 μl |
| 50% | 50 μl | 50 μl |
| 100% | 0 μl | 100 μl |

Preparation of Biotynylated Normal Gene

Gene amplification by PCR was conducted under the conditions as described above by using pSK-2 (the plasmid containing the normal gene) as described above for the template and 100 ng each of Bio-PHR-1 and Bio-CHRAS-1 as described below having biotin introduced in their 5' end as the label capable of binding to the solid support. The resulting amplification product was electrophoresed on agarose gel to confirm the size of the amplified product and the amplification rate. The resulting amplification product is the biotynylated normal gene.

Bio-PHR-1

Biotin-5'ATGACGGAATATAAGCTGGTG3'    (SEQ ID NO: 1)

Bio-CHRAS-1

Biotin-5'CTGGATGGTCAGCGCACTCTT3'    (SEQ ID NO: 2)

Concentration Step

1 μl of the test samples as described above of various mixing ratio were amplified by PCR under the conditions as described above by using 100 ng each of $NH_2$-PHR-1 and $NH_2$-CHRAS-1 as described above for the primers. The amplification product was diluted 10 times with distilled water, and 5 μl of the dilution product was mixed with 5 μl of the biotynylated normal gene amplification product, 10 μl of 10×SSC (10×SSC: 0.3 M sodium citrate, pH 7.0, 0.3 M sodium chloride) and 10 μl of distilled water. In other words, the test sample was mixed with 10 times as much biotynylated normal gene amplification product. The Solution was heated to 98° C. for 10 minutes for thermal denaturation. The temperature was then reduced from 98° C. to 70° C. at a very gentle temperature gradient of 1° C. per 10 minutes for the formation of double strand (competitive hybridization).

The reaction solution was diluted by adding 80 μl of TE buffer (10 mm Tris-HCl buffer (pH 8.0), 1 mM EDTA), and the thus diluted solution was added to a well having streptavidin immobilized thereon. After shaking for 15 minutes at room temperature, the reaction solution was sucked and transferred to a new well. The plate was shaken for another 15 minutes at room temperature. 1 μl of the reaction solution was amplified by PCR under the conditions as described above by using 100 ng each of $NH_2$-PHR-1 and $NH_2$-CHRAS-1 as described above for the primers. 10 μl of the resulting solution was treated with restriction enzyme HpaII (this restriction enzyme HpaII cleaves normal gene but not the mutant gene).

Detection

The reaction solution was subjected to polyacrylamide gel electrophoresis to analyze the resulting DNA fragments in comparison with those before the concentration step. The results are shown in Table 2.

TABLE 2

| % of mutant gene | Before concentration | | After concentration | |
|---|---|---|---|---|
| | Normal gene | Mutant gene | Normal gene | Mutant gene |
| 0% | ++ | − | ++ | − |
| 10% | ++ | − | + | ++ |
| 50% | ++ | ++ | − | ++ |
| 100% | − | ++ | − | ++ |

++: Clear band was detectable.
+: Unclear, ambiguous band was detectable.
−: Band was undetectable.

As shown in the results of Table 2, in the sample containing 10% of the mutant gene, the band of about 60 bp corresponding to the mutant gene which was scarcely observed in the sample before the concentration step was clearly seen. In the sample containing 50% of the mutant gene, the band of about 30 bp corresponding to the normal gene which was clearly observed in the sample before the concentration step substantially disappeared through the concentration step, and the band of about 60 bp corresponding to the mutant gene could be reliably confirmed. These facts confirm that the concentration method of the present invention is capable of selectively concentrating the mutant gene from the mixture of the normal gene and the mutant gene. It should be noted that the percentage of the mutant gene can be increased to a further extent by repeating the series of concentration steps as described above.

EXAMPLE 2 mRNA was extracted from a pancreas tissue sample containing pancreatic cancer cells including both normal Ki-ras gene from the cancer cell and mutant Ki-ras gene wherein GGT (Gly) of the 12th codon has been substituted with GAT (Asp). The process for concentrating the mutant gene from such mRNA is described below.

Preparation of Nucleic Acid Sample mRNA was extracted from the pancreas tissue by using Quick Prep mRNA Purification Kit (Pharmacia). By using the thus extracted mRNA for the template, cDNA was prepared through reverse transcription by the procedure as described below.

The reverse transcription was conducted at 37° C. for 30 minutes in the presence of 20 µl of 10 mM Tris-HCl buffer (pH 8.3) containing 1 µm of mRNA, 2 mM $MgCl_2$, 0.01% gelatin, 1 mM each of dATP, dGTP, dCTP and dTTP, and 20 units of placental RNase inhibitor by using 5 µg of oligo $(dT)_{12-18}$ for the primer and 100 units of murine reverse transcriptase to obtain cDNA (cDNA solution). The cDNA solution was heated to 95° C. for 5 minutes to inactivate the enzyme.

Next, the cDNA solution as described above was used for the PCR according to the procedure as described below.

To 20 µl of the cDNA solution were added 80 µl of 10 mM Tris-HCl buffer (pH 8.3), 50 mM KCl, 1.5 mM $MgCl_2$, 0.01% gelatin, and 2 units of Taq DNA polymerase in the presence of 200 µM each of dATP, dGTP, dCTP, and dTTP. 10 pmol each of $NH_2$-KRASF and $NH_2$-KRASR as described below were used for the primers. The solution was overlaid with mineral oil.

The solution was heated to 94° C. for 5 minutes, and 30 cycles of 30 sec. at 94° C., 30 sec. at 60° C., and 60 sec. at 72° C. were repeated for amplification to prepare the nucleic acid sample.

$NH_2$-KRASF $NH_2$-5'AACTTGTGGTAGTTGGACCT3' (SEQ ID NO: 3)

$NH_2$-KRASR $NH_2$-5'CTATTGTTGGATCATATTCG3' (SEQ ID NO: 4)

Preparation of Labeled Nucleic Acid Standard

The labeled nucleic acid standard was prepared by the procedure as described below.

Chromosomal DNA was extracted from 500 µl of blood collected from a normal donor by using SepaGene (manufactured by Sanko Pure Chemicals). Of the thus extracted DNA, 500 ng portion was used for the template, and 2 units of Taq DNA polymerase was added in the presence of 100 µl of 10 mM Tris-HCl buffer (pH 8.3), 50 mM KCl, 1.5 mM $MgCl_2$, 200 µM each of dATP, dGTP, dCTP, and dTTP using 10 pmol each of Bio-KRASF and Bio-KRASR as described below for the primers. The solution was overlaid with mineral oil. The solution was heated to 94° C. for 5 minutes, and 30 cycles of 30 sec. at 94° C., 30 sec. at 60° C., and 60 sec. at 72° C. were repeated for amplification to prepare the labeled nucleic acid standard.

Bio-KRASF

Biotin-5'AACTTGTGGTAGTTGGACCT3' (SEQ ID NO: 3)

Bio-KRASR

Biotin-5'CTATTGTTGGATCATATTCG3' (SEQ ID NO: 4)

Concentration Step

First Concentration Step

The nucleic acid sample as described above was diluted 10 times with distilled water, and 5 µl of the dilution product was mixed with 5 µl of the labeled nucleic acid standard (biotynylated normal gene amplification product), 10 µl of 10×SSC, and 10 µl of distilled water. In other words, the nucleic acid sample was mixed with 10 times as much biotynylated normal gene amplification product. The solution was heated to 98° C. for 10 minutes for thermal denaturation. The temperature was then reduced from 98° C. to 70° C. at a very gentle temperature gradient of 1° C. per 10 minutes for hybridization. The reaction solution was diluted by adding 80 µl of TE buffer, and the thus diluted solution was added to a well having streptavidin immobilized thereon. After shaking for 15 minutes at room temperature, the reaction solution was sucked and transferred to a new well. The plate was shaken for another 15 minutes at room temperature.

1 µl of the resulting reaction solution was amplified by PCR under the conditions as described above by using 100 ng each of $NH_2$-KRASF and $NH_2$-KRASR as described above for the primers. 10 µl of the reaction solution was treated with restriction enzyme BstNl (this restriction enzyme BstNl cleaves normal gene but not the mutant gene). The reaction solution was subjected to polyacrylamide gel electrophoresis to analyze the resulting DNA fragments. The residual solution was subjected to the second concentration step as described below.

Second and Later Concentration Steps

The PCR amplification product obtained in the first concentration step as described above was diluted 10 times with distilled water, and 5 µl of the dilution product was mixed with 5 µl of the labeled nucleic acid standard (biotynylated normal gene amplification product), 10 µl of 10×SSC, and 10 µl of distilled water. As in the case of the first concentration step, the solution was subjected to thermal denaturation, annealing by temperature gradient, PCR amplification, and digestion with the restriction enzyme. The thus obtained DNA fragments were analyzed as in the case of the first concentration step. The residual solution was subjected to another step of concentration by repeating the procedure as described above. After the treatment with the restriction enzyme, the resulting DNA fragments were analyzed by the procedure as described above.

The results for the detection of the mutant gene and the normal gene in each step are shown in Table 3.

TABLE 3

| Number of concentration | Normal gene | Mutant gene |
| --- | --- | --- |
| No concentration step | ++ | − |
| 1 concentration step | ++ | + |
| 2 concentration steps | ++ | + |
| 3 concentration steps | + | ++ |

++: Clear band was detectable.
+: Unclear, ambiguous band was detectable.
−: Band was undetectable.

As shown in the results of Table 3, the concentration method of the present invention is capable of selectively concentrating the mutant gene even if the target nucleic acid is mRNA. It was also confirmed that the concentration method of the present invention is capable of reliably increasing the percentage of the mutant gene by repeating the concentration step.

EXAMPLE 3

Another method of concentrating the mutant nucleic acid is described below. This method is conducted by using the labeled nucleic acid sample prepared from the nucleic acid sample by using two types of labeled primers and the unlabeled nucleic acid standard.

Preparation of Labeled Nucleic Acid Sample mRNA was extracted from the pancreatic tissue by repeating the procedure of Example 2, and cDNA was obtained from the mRNA by reverse transcription. PCR reaction was conducted by using the cDNA solution in accordance with the procedure as described below.

10 pmol each of Bio-KRASF and DNP-KRASR as described below were used for the primers, and to 20 µl of the cDNA solution were added 80 mM Tris-HCl buffer (pH 8.3), 50 mM KCl, 1.5 mM $MgCl_2$, 0.01% of gelatin, and 2 units of Taq DNA polymerase in the presence of 200 µM each of dATP, dGTP, dCTP, and dTTP. The solution was overlaid with mineral oil. The solution was heated to 94° C. for 30 seconds, and 30 cycles of 30 sec. at 94° C., 30 sec. at 60° C., and 60 sec. at 72° C. were repeated for amplification to prepare the labeled nucleic acid sample.

Bio-KRASF

Biotin-5'AACTTGTGGTAGTTGGACCT3'    (SEQ ID NO: 3)

DNP-KRASR

DNP-5'CTATTGTTGGATCATATTCG3'    (SEQ ID NO: 4)

Preparation of Nucleic Acid Standard

The nucleic acid standard was prepared by the procedure as described below.

Chromosomal DNA was prepared from the normal blood as in the case of Example 2, and the DNA was amplified under the conditions similar to the nucleic acid sample as describe above by using 10 pmol each of $NH_2$-KRASF and $NH_2$-KRASR to prepare the nucleic acid standard.

$NH_2$-KRASF $NH_2$-5'AACTTGTGGTAGTTGGACCT3'    (SEQ ID NO: 3)

$NH_2$-KRASR $NH_2$-5'CTATTGTTGGATCATATTCG3'    (SEQ ID NO: 4)

Concentration Step

First Concentration Step

The labeled nucleic acid sample as described above was diluted 100 times with distilled water, and 5 µl of the dilution product was mixed with 5 µl of the nucleic acid standard, 10 µl of 10×SSC, and 10 µl of distilled water. In other words, the labeled nucleic acid sample was mixed with 100 times as much unlabeled nucleic acid having the normal sequence. The solution was heated to 98° C. for 10 minutes for thermal denaturation. The temperature was then reduced from 98° C. to 70° C. at a very gentle temperature gradient of 1° C. per 10 minutes for hybridization. The reaction solution was diluted by adding 80 µl of TE buffer, and the thus diluted solution was added to a well having streptavidin immobilized thereon. After shaking for 15 minutes at room temperature, the reaction solution was sucked and transferred to a new well. The plate was shaken for another 15 minutes at room temperature, and the reaction solution was removed by suction. The well was washed three times with 300 µl of TE buffer.

Next, 10 µl of 0.01 N NaOH was added to the well for denaturation of the nucleic acid adsorbed on the well. The supernatant was collected in order to gather the single strand nucleic acid of the type without biotin label. The thus collected solution was neutralized by adding 10 µl 0.1 M Tris-HCl buffer (pH 7.0), 150 mM NaCl and 1 mM EDTA.

To this solution were added magnet beads which had been modified with sheep anti-rabbit IgG antibody (DYNABEADS™ M-280, Sheep anti-rabbit IgG, DYNAL Inc.) to collect DNA-labeled single strand nucleic acid sample/rabbit anti-DNP antibody/sheep anti-rabbit IgG antibody-modified magnet bead complex by using a magnet. The thus collected complex was washed three times with 300 µm 0.1 M Tris-HCl buffer (pH 7.0), 150 mM NaCl, and 1 mM EDTA.

The complex was then suspended in 30 µl of 0.1 M Tris-HCl buffer (pH 7.0), 150 mM NaCl, and 1 mM EDTA, and the suspension was heated to 98° C. for 5 minutes to inactivate the antibody molecule. The magnet beads were removed by using a magnet, and the supernatant containing the DNP-labeled single strand nucleic acid sample was collected.

1 µl of the resulting supernatant was amplified under the conditions as employed in the preparation of the labeled nucleic acid sample by using Bio-KRASF and DNP-KRASR for the primers. 10 µl of the reaction solution was treated with restriction enzyme BstNI (this restriction enzyme BstNI cleaves normal gene but not the mutant gene). The reaction solution was subjected to polyacrylamide gel electrophoresis to analyze the resulting DNA fragments. The residual solution was subjected to the second concentration step as described below.

Second and Later Concentration Steps

The PCR amplification product obtained in the first concentration step as described above was diluted 100 times with distilled water, and 5 µl of the dilution product was mixed with 5 µl of the above-described nucleic acid standard, 10 µl of 10×SSC, and 10 µl of distilled water. As in the case of the first concentration step, the solution was subjected to thermal denaturation, annealing by temperature gradient, adsorption on the solid support, PCR amplification, and digestion with the restriction enzyme. The thus obtained DNA fragments were analyzed as in the case of the first concentration step. The residual solution of the second concentration step was subjected to another step of concentration by repeating the procedure as described above, and the resulting DNA fragments were analyzed by the procedure as described above.

The results for the detection of the mutant gene and normal gene in each step are shown in Table 4.

TABLE 4

|  | Normal gene | Mutant gene |
| --- | --- | --- |
| No concentration step | ++ | − |
| 1 concentration step | ++ | + |
| 2 concentration steps | + | ++ |
| 3 concentration steps | + | ++ |

++: Clear band was detectable.
+: Unclear, ambiguous band was detectable.
−: Band was undetectable.

As shown in the results of Table 4, this concentration method is capable of selectively separating and collecting the mutant nucleic acid from the sample including both the nucleic acid wherein the particular segment of the nucleic acid comprises the normal gene and the mutant nucleic acid having a nucleotide sequence slightly different from the normal gene. A minute amount of mutant nucleic acid in the sample is thereby detected.

contain said mutant sequence, said method comprising the following steps:

(1) preparing a nucleic acid sample by amplifying said particular segment of said target sequence of said first and second nucleic acids,

---

---

I claim:

1. A method for selectively concentrating a first nucleic acid from a sample containing said first nucleic acid and at least a second nucleic acid, wherein said first nucleic acid comprises a particular segment of a target sequence, said target sequence of said first nucleic acid containing a mutant sequence, and said second nucleic acid comprises the particular segment of said target sequence, with the exception that the target sequence of said second nucleic acid does not (2) adding to said nucleic acid sample an equimolar amount or more of a labeled nucleic acid standard prepared by incorporating a label capable of binding to a solid support into a nucleic acid having a nucleotide sequence complementary to the particular segment of said second nucleic acid, (3) performing a competitive hybridization after said adding step (2), and (4) separating and removing a hybridizate having said label capable of binding to the solid support and the residual labeled nucleic acid standard in the reaction solution after the competitive hybridization by trapping said hybridizate having said label and the residual labeled nucleic acid standard on the solid support, wherein,
(i) steps (1) to (4) are sequentially performed one or more times, or
(ii) steps (1) to (4) are sequentially performed once and then steps (2) to (4) are sequentially performed one or more times.

2. The method for concentrating a first nucleic acid according to claim 1, wherein said nucleic acid sample is a single strand or double strand DNA prepared by amplifying said particular segment of said target sequence of said first and second nucleic acids by means of PCR using primers.

3. The method for concentrating a first nucleic acid according to claim 1 or 2, wherein said labeled nucleic acid standard is a single strand or double strand DNA prepared by amplifying a nucleic acid standard having a nucleotide sequence complementary to the particular segment of said second nucleic acid, by means of PCR using primers having the label capable of binding to a solid support incorporated herein.

4. The method for concentrating a first nucleic acid according to claim 1 or 2, wherein said labeled nucleic acid standard is a single strand or double strand DNA prepared by a host/vector system selected from the group consisting of a plasmid vector, a phage vector, and a chimeric vector of a plasmid and a phage, wherein said DNA has the label capable of binding to a solid support incorporated therein.

5. The method for concentrating a first nucleic acid according to claim 1, wherein biotin is used for said label capable of binding to a solid support, and avidin or streptavidin is used for the binding site of the solid support.

6. The method for concentrating a first nucleic acid according to claim 1, wherein said first and second nucleic acids are cDNAs obtained by transcribing the corresponding mRNAs with a reverse transcriptase, and said nucleic acid sample is prepared by amplifying the cDNA.

7. A method for selectively concentrating a first nucleic acid from a sample containing said first nucleic acid and at least a second nucleic acid, wherein said first nucleic acid comprises a particular segment of a target sequence, said target sequence of said first nucleic acid containing a mutant sequence, and said second nucleic acid comprises the particular segment of said target sequence, with the exception that the target sequence of said second nucleic acid does not contain said mutant sequence, said method comprising the following steps:
(1) preparing a labeled nucleic acid sample by amplifying said particular segment of said target sequence of said first and second nucleic acids, and simultaneously, incorporating two types of labels respectively capable of binding to solid supports into the amplification product,
(2) adding to said labeled nucleic acid sample an equimolar amount or more of a nucleic acid standard having a nucleotide sequence complementary to the particular segment of said second nucleic acid,
(3) performing a competitive hybridization after said adding step (2),
(4) collecting the hybridizates having one of said two types of labels from the reaction solution after the competitive hybridization by trapping such hybridizates on the first solid support which selectively binds to said one of said two labels, and
(5) collecting the hybridizates having both of said two types of labels by contacting the hybridizates collected in the step (4) with the second solid support which selectively binds to the other one of the two labels wherein,
(i) steps (1) to (5) are sequentially performed one or more times, or
(ii) steps (1) to (5) are sequentially performed once and then steps (2) to (5) are sequentially performed one or more times.

8. The method for concentrating a first nucleic acid according to claim 7, wherein said labeled nucleic acid sample is prepared by amplifying said particular segment of said target sequence of said first and second nucleic acids by PCR using a primer having said first label incorporated therein and a primer having said second label incorporated therein.

9. The method for concentrating a first nucleic acid according to claim 7 or 8, wherein biotin and a hapten are respectively used for said first and second labels, and avidin or streptavidin and an antibody are respectively used for binding sites of said first and second solid supports.

10. The method for concentrating a first nucleic acid according to claim 7, wherein said nucleic acid standard is a single strand or double strand DNA prepared by amplifying a nucleic acid standard having a nucleotide sequence complementary to the particular segment of said second nucleic acid by means of PCR using primers.

11. The method for concentrating a mutant nucleic acid according to claim 7, wherein said nucleic acid standard is a single strand or double strand DNA prepared by a host/vector system selected from the group consisting of a plasmid vector, a phage vector, and a chimeric vector of a plasmid and a phage.

12. The method for concentrating a first nucleic acid according to claim 7, wherein said first and second nucleic acids are cDNAs obtained by transcribing the corresponding mRNAs with a reverse transcriptase, and said nucleic acid sample is prepared by amplifying the cDNA.

13. A method for selectively concentrating a first nucleic acid from a sample containing said first nucleic acid and at least a second nucleic acid, wherein said first nucleic acid comprises a particular segment of a target sequence, said target sequence of said first nucleic acid containing a mutant sequence, and said second nucleic acid comprises the particular segment of said target sequence, with the exception that the target sequence of said second nucleic acid does not contain said mutant sequence, said method comprising the following steps:
(1) preparing a labeled nucleic acid sample by amplifying said particular segment of said target sequence of said first and second nucleic acids, and simultaneously, incorporating two types of labels respectively capable of binding to solid supports into the amplification product,
(2) adding to said labeled nucleic acid sample an equimolar amount or more of a nucleic acid standard having a nucleotide sequence complementary to the particular segment of said second nucleic acid,
(3) performing a competitive hybridization after said adding step (2),
(4) collecting the hybridizates having one of said two types of labels from the reaction solution after the competitive hybridization by trapping such hybridizates on the first solid support which selectively binds to said one of said two labels,
(5) preparing single strand nucleic acids by denaturing of the hybridizates collected in step (4), and
(6) collecting the single strand nucleic acids having the other one of said two types of labels by contacting the single strand nucleic acids with the second solid support which selectively binds to the other one of the labels, wherein,
(i) steps (1) to (6) are sequentially performed one or more times, or
(ii) steps (1) to (6) are sequentially performed once and then steps (2) to (6) are sequentially performed one or more times.

14. An assay kit for concentrating a first nucleic acid by the method of claim 13, wherein said kit comprises:

labeled nucleic acid sample-preparing reagents for preparing the labeled nucleic acid sample by amplifying the particular segment of the target sequence of said first and second nucleic acids, and simultaneously, incorporating two types of labels into the amplified product;

nucleic acid standard having a nucleotide sequence complementary to the particular segment of the second nucleic acid;

a first solid support having a site which is capable of binding to one of said two types of labels;

a reagent for denaturing the hybridizates into single strand nucleic acids;

magnet beads having a site which is capable of binding to the other one of said two types of labels; and a magnet for recovering the magnet beads from the reaction solution.

15. An assay kit for concentrating a first nucleic acid by the method of claim 8, wherein said kit comprises:

labeled nucleic acid sample-preparing reagents including two types of labeled primers prepared by incorporating different labels into two types of primers capable of amplifying the particular segment of the target sequence of said first and second nucleic acids;

nucleic acid standard-preparing reagents which are capable of amplifying the nucleic acid standard having a nucleotide sequence complementary to the particular segment of the second nucleic acid;

a first solid support having a site which is capable of binding to one of said two types of labels; and a second solid support having a site which is capable of binding to the other one of said two types of labels.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: 5' end is modified with NH2 or Biotin

<400> SEQUENCE: 1
atgacggaat ataagctggt g                                               21

<210> SEQ ID NO 2
<211> LENGTH: 21
<212> TYPE: DNA
<213> ORGANISM: Homo sapiens
<220> FEATURE:
<221> NAME/KEY: misc_feature
<222> LOCATION: (1)..(20)
<223> OTHER INFORMATION: 5' end is modified with NH2 or Biotin

<400> SEQUENCE: 2
ctggatggtc agcgcactct t                                               21

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: 5' end is modified with NH2 or Biotin

<400> SEQUENCE: 3
aacttgtggt agttggacct                                                 20

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: 5' end is modified with NH2 or Biotin or DNP

<400> SEQUENCE: 4
ctattgttgg atcatattcg                                                 20
```